(12) United States Patent
Torrison

(10) Patent No.: US 6,427,543 B1
(45) Date of Patent: Aug. 6, 2002

(54) VENTURI-BASED GAS SAMPLING MANIFOLD

(75) Inventor: Eric Torrison, 6518 44th Ave. SW., Seattle, WA (US) 98136-1704

(73) Assignee: Eric Torrison, Seattle, WA (US)

( * ) Notice: Subject to any disclaimer, the term of this patent is extended or adjusted under 35 U.S.C. 154(b) by 0 days.

(21) Appl. No.: 09/816,595

(22) Filed: Mar. 23, 2001

(51) Int. Cl.[7] .................................................. G01N 1/00
(52) U.S. Cl. .................................. 73/863.33; 73/863.83
(58) Field of Search ........................ 73/863.33, 863.83, 73/864.32, 864.73

(56) References Cited

U.S. PATENT DOCUMENTS

| | | | | |
|---|---|---|---|---|
| 2,814,952 A | * | 12/1957 | Ryant, Jr. et al. | 73/863.33 |
| 3,468,166 A | * | 9/1969 | Putman | 73/864.34 |
| 3,736,792 A | * | 6/1973 | Poulsen | 73/863.33 |
| 4,090,392 A | * | 5/1978 | Smith et al. | 73/863.33 |
| 4,150,575 A | | 4/1979 | Wolf | 73/421.5 |
| 5,184,501 A | | 2/1993 | Lewis et al. | 73/23.31 |
| 5,337,595 A | | 8/1994 | Lewis | 73/23.31 |
| 5,423,228 A | * | 6/1995 | Budd et al. | 73/864.73 |
| 5,469,791 A | | 11/1995 | Decker et al. | 73/23.31 |
| 5,604,319 A | | 2/1997 | Kohsaka et al. | 73/863.11 |
| 5,691,703 A | | 11/1997 | Roby et al. | 340/628 |
| 5,869,344 A | | 2/1999 | Linforth et al. | 436/173 |
| 6,062,092 A | | 5/2000 | Weaver | 73/863.03 |
| 6,181,250 B1 | | 1/2001 | Brooks, Jr. | 340/577 |

* cited by examiner

*Primary Examiner*—Robert Raevis
(74) *Attorney, Agent, or Firm*—Black Lowe & Graham PLLC

(57) ABSTRACT

The present invention comprises a system and method for extracting and conveying sampling gases from a remote location for component and quality testing by a gas-sampling device by use of a venturi-based manifold that moves a volume of motivating gases to create a venturi effect. The venturi-based gas sampling manifold includes an air extractor assembly having an inlet port with an associated inlet valve for selectively interrupting the flow of gas through the inlet port, a venturi connected on one end to a venturi jet and on the other end to a venting horn, and a plenum extending from the inlet port to the available end of the venturi. The present system further includes a sampling manifold assembly having a manifold in which the plenum of the air extractor assembly is carried, one or more manifold ports with associated manifold port valves for selectively adjusting the flow rate through the manifold port, and one or more sampling ports. In operation, the venturi air extractor generates a vacuum according to Bernoulli's equations. Selective opening of the manifold ports on the manifold along with the application of vacuum draws sampling gases from remote locations through probes and the associated connecting hoses to the manifold. Once the suspect sampling gases, drawn through the appropriate probe, fill the manifold, the operator eliminates the vacuum and the drawn sample gases are available for testing at the sampling port. After testing, the operator reapplies the vacuum and flushes the sampling gases.

15 Claims, 2 Drawing Sheets

VENTURI-BASED GAS SAMPLING MANIFOLD

FIELD OF THE INVENTION

The instant invention teaches a system and method of extracting and conveying gases for sampling.

BACKGROUND OF THE INVENTION

Any confined space in an industrial setting presents an insidious hazard to workers. A confined space is a defined volume that has limited openings for entry and exit and unfavorable natural ventilation. Such confined spaces may contain dangerous air contaminants such as toxic or inert environmental gases that will poison or suffocate an exposed worker. Examples of confined spaces in industrial settings include but are not limited to storage tanks, compartments of ships, process vessels, pits, silos, vats, wells, sewers, digesters, degreasers, reaction vessels, boilers, ventilation and exhaust ducts, tunnels, underground utility vaults, and pipelines.

The failure to recognize and control the hazards associated with confined spaces quite often results in injury or fatality to those who rush to the aid of workers exposed to such environments. Without knowledge of the composition of the environment, would-be rescuers are themselves at risk for injury. Generally, these environmental gases are invisible or barely visible as vapors; rescuers have nothing to warn them of the danger.

Normal atmosphere is composed of approximately 21% oxygen, 78% nitrogen, and 1% argon, with small amounts of various other gases. Individuals begin to suffer oxygen deprivation, or hypoxia, when the oxygen level drops below 17%. The first sign of hypoxia is a deterioration of night vision, generally not noticed by the victim. When oxygen levels fall to between 14% and 16%, physiologic effects include increased breathing volume, accelerated heartbeat, poor muscular coordination, rapid fatigue, and intermittent respiration. When oxygen levels fall to between 6% and 10%, the effects on a victim are nausea, vomiting, inability to perform, and unconsciousness. At concentrations less than 6%, the result is rapid loss of consciousness and death in minutes.

Any number of regular industrial processes can serve to foul the atmosphere by consuming oxygen. Welding, cutting, or brazing each consumes oxygen. Bacterias found in swamps and landfills and yeasts present in baking consume oxygen. Even a slow chemical reaction such as the rusting of exposed surfaces of metal tanks, vats, and ship holds consume oxygen.

Displacement of oxygen by inert gases can be equally fatal. Any gas with a different mass per volume than oxygen will displace the oxygen in the environment. Carbon dioxide, propane, argon, and helium, none of them toxic, will asphyxiate a worker by displacing necessary oxygen.

Where a fuel is present in the atmosphere, as results from the vaporization of flammable liquids, as by-products of chemical reaction, in enriched oxygen atmospheres, or in concentrations of combustible dusts, the presence rather than the absence of oxygen presents the principal hazard. Fuel and oxygen in the proper atmospheric mixture will combust explosively in the presence of a source of ignition. Any ignition source will do—a spark from a motor or the flame of a welding torch. A typical industrial setting is rich with ignition sources.

The proper or stoichiometric proportion of oxygen to gas for combustion will vary from gas to gas. The inherent properties of a gas fix a range defined as the lower flammability limit (LFL) and upper flammability limit (UFL) or lower explosive limit (LEL) and upper explosive limit (UEL), respectively. The explosive range for methane is, for example, between 5% and 15% in air. Concentrations below 5% methane are below the explosive range, and concentrations above 15% are too rich to support combustion. Where a confined space contains methane in, for example, a 27% concentration, the introduction of air will dilute the methane, making the formerly inert atmosphere explosive.

Firefighters responding to an industrial fire present themselves to far greater danger than might exist absent the fire. The heat of a fire vaporizes otherwise stable solvents, efficiently distributing flammable and likely toxic gases into the environment. Fire also removes oxygen from the atmosphere, thus dynamically shifting ratios of oxygen to fuel in the environment, possibly through the explosive range. By-products of combustion may themselves be toxic, or simply heavy enough to displace the oxygen in the environment.

Should the industrial fire be aboard a commercial vessel, the presence of a far greater number of confined spaces than might be present in a land-based industrial setting multiplies the dangers inherent in an industrial fire. Because the hull of a ship is not a strictly rectilinear form, the hull's function compromises the shape of industrial workspaces aboard. The industrial functions aboard a vessel requires further compromises in hull design, resulting in tortuous passageways, multiple distinct and confined compartments, and a funnel-shaped skin of the hull, well-suited to directing heavy gases to the bowels of the ship.

In light of the many compartments susceptible to the collection of asphyxiating, flammable, or toxic gases in industrial and shipboard settings, whether during a fire or in the course of day-to-day operation, it is important to be able to sample gases within any confined space prior to entry. The Occupational Safety and Health Administration requires such sampling in regulation D94-01-048 entitled, "Sampling for Confined Space Entry." 29 CFR 1910.146(c)(5)(ii)(C). While such regulation does not bind firefighters and other emergency rescue workers (29 CFR 1910.146(k)), the potential for hazard and thus the need for sampling in this context is even greater.

Traditional gas sampling in industrial settings typically involves handheld devices including a blower, a short plenum, and chamber for sampling. One such sampling device, the LeakAlert™, has, for instance, a 20-inch probe. This device conducts a sample of ambient air through the probe, exhausting the same at the far end of the chamber. Using this type of handheld device to detect ambient gases requires that the operator be within the environment tested. Moreover, using the same device to test air within a closed compartment, from the outside, acts to introduce the suspect gases into the operator's own environment. Where the suspect gases turn out to be a fuel, this introduction may bring the level of gases in the ambient environment to explosive levels.

Yet another disadvantage with the prior art handheld devices relates to how potentially hazardous gases are ported to the ambient atmosphere from the system after testing. Traditional systems have used an aspirator bulb to draw a gaseous sample into contact with the atmospheric tester. Hand-operated aspirator bulb equipment therefore requires much effort to purge a lengthy hose and draw a proper sample from a confined space.

In light of the noted hazards and the above-identified disadvantages with the existing systems, important criteria emerge as necessary for the safe operation of a gas sampling system. First, a safe apparatus for gas sampling should be capable of exhausting the sample a safe distance from the operator or operators and should do so in an environment where the exhausted sample will readily dissipate. Second, the gas sampling apparatus must remove any ignition source from contact with the drawn sample; electric motors and compressors should be isolated from the gas-sampling stream. Third, the intake port for the apparatus must be portable to assure that sampling will take place at each level that workers will enter. A ponderous apparatus would prevent use in the tortuous passageways common in industrial settings. Good confined space sampling equipment comes with probes that operators can lower into the space.

SUMMARY OF THE INVENTION

The present invention comprises a system and method for extracting and conveying sampling gases from a remote location for component and quality testing by a gas-sampling device by use of a venturi-based manifold that moves a volume of motivating gases to create a venturi effect. The system includes an air extractor for creating a vacuum to draw sampling gases for testing. The air extractor includes a venturi having an inlet end and an outlet end, the inlet end further connected to a venturi jet through which the volume of motivating gas is drawn to create a venturi effect and the outlet end further connected to a horn through which motivating gases are vented to the atmosphere, an inlet port having a means for selectively interrupting the flow of motivating gases through the inlet port into the plenum, and a plenum extending from the inlet port to the inlet end of the venturi. The system includes a sampling manifold for testing the sampling gases drawn by the air extractor. The sampling manifold includes a housing defining a chamber in which the plenum of the air extractor is located, at least one manifold port through which the sampling gases from the remote location are drawn into the housing by the venturi effect created by the air extractor, the manifold port having a means for selectively interrupting the flow of sampling gases through the manifold port into the manifold, and at least one sampling port through which a sample of the sampling gases drawn by the air extractor into the housing of the manifold are drawn by the gas-sampling device, the sampling port having a means for selectively controlling the sample of sampling gases from the manifold to the gas-sampling device.

In an alternative embodiment, the system further includes a pressure gauge for monitoring and reporting the pressure of the gases within the manifold.

In alternative embodiments, the system further includes a temperature gauge for monitoring and reporting the temperature of the gases within the manifold.

In an alternative embodiment, the air extractor further includes a regulator assembly used to control the operation of the venturi. The regulator assembly includes a needle piston movably positioned with respect to the venturi that is used to control the volume of motivating gas that flows through the venturi and a regulator spring connected to the needle piston for adjusting the needle piston with respect to the venturi to optimize the flow of motivating gas and create the greatest vacuum with the least expenditure of motivating gas.

In an alternative embodiment, the sampling manifold includes an adjustable manifold plate between the manifold and the manifold port, the manifold plate having a hole that can be aligned between the manifold and the manifold port to allow flow of sampling gases from the manifold port into the manifold.

The method of the present invention includes the following steps: feeding high-pressure motivating gases through a venturi to create a venturi effect; extracting and conveying sampling gases from a remote location by use of the venturi effect created by the venturi; drawing sampling gases into a manifold through a manifold port; testing samples of the sampling gases from the manifold using the gas-sampling device; and venting the sampling gases from the manifold.

In an alternative embodiment, the sampling gases are extracted and conveyed from a remote location into the manifold via a manifold port, and the step of extracting and conveying sampling gases from a remote location by use of the venturi effect created by the venturi further includes selectively interrupting the flow of sampling gases through the manifold port into the manifold using a manifold port valve.

In an alternative embodiment, the step of feeding high-pressure motivating gases through a venturi to create a venturi effect further includes controlling the operation of the venturi by positioning a needle piston movably with respect to the venturi to control the volume of motivating gas that flows through the venturi and create the greatest vacuum with the least expenditure of motivating gas.

Alternative embodiments of the present method further includes monitoring and reporting the pressure and temperature of the gases within the manifold by use of pressure and temperature gauges, respectively.

BRIEF DESCRIPTION OF THE DRAWINGS

The preferred embodiment of the present invention is described in detail below with reference to the following drawings.

DETAILED DESCRIPTION OF THE PREFERRED EMBODIMENT

By way of overview, the system of the present invention includes in combination an air extractor assembly 10 and a sampling manifold assembly 30. A high-pressure gas feed creates a vacuum in the air extractor that draws gases into the sampling manifold. Once the gas is in the manifold, the operator removes the vacuum and the manifold contains those gases until a commercially available gas sampler can draw them out for analysis. The air extractor operates because of Bernoulli's principle and the equations that follow therefrom. Simply stated, Bernoulli's principle is that where there is slow flow in a fluid, you will find increased pressure and, conversely, where there is increased flow in a fluid, you will find decreased pressure. Releasing high-pressure gases into a narrowed passage or venturi of the air extractor causes a high-velocity flow and a resultant low-pressure area, or a partial vacuum. The air extractor vents the vacuum to the manifold. This vented vacuum is sufficient to draw gases through the sampling manifold. A series of valves selectively expose hoses to the vacuum drawing gases from remote locations for sampling.

Figure 1:
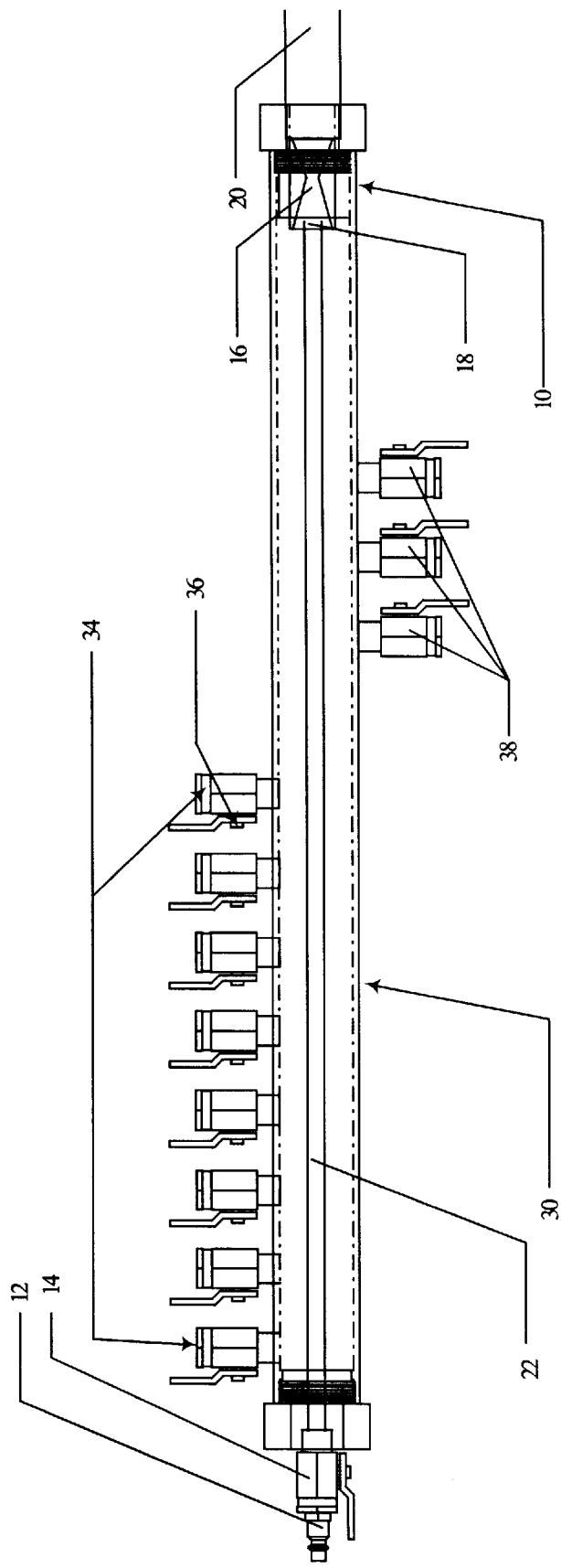
FIG. 1 is a first embodiment of the present invention.

A preferred embodiment of a venturi-based gas-sampling manifold of the present invention is described with reference to FIG. 1. Air extractor assembly 10 includes an inlet port 12 with an associated inlet valve 14 for selectively interrupting the flow of gas through the inlet port, a venturi 16 connected on one end to a venturi jet 18 and on the other end to a horn 20, and a plenum 22 extending from the inlet port to the available end of venturi jet 18. Sampling manifold assembly 30 includes a manifold 32 in which plenum 22 of the air extractor assembly is carried, one or more manifold ports 34 with associated manifold port valves 36 for selectively adjusting the flow rate through the manifold port, and one or more sampling ports 38. It will be appreciated by those skilled in the art that the location and number of manifold ports and sampling ports may vary without departing from the scope of the present invention.

When in use, an operator feeds high-pressure gas through inlet port 12. The operator may selectively interrupt the flow of the high-pressure gas with the inlet valve 14. High-pressure gas flows through the inlet valve and continues through plenum 22 and into venturi jet 18. In some applications such as fire fighting, plenum 22 may also serve to collect heat from the space within the body of sampling manifold 30, thereby imparting additional kinetic energy to the gas flow through the venturi jet as the heat expands the high pressure gas. Venturi jet 18 vents into the throat of venturi 16, and then into horn 20, which functions as a means for finally venting the high-pressure feed gas to the atmosphere. In an alternative embodiment, the throat of the venturi might include a long low restriction exhaust hose. The exhaust hose would conduct the mix of motive and suction gas to a location that is remote from the operators or might assure optimum dissipation of that mixture. By conducting the gas mixture to a remote site, the use of the invention assures the safety of the operators. The rapid flow of gases through the venturi creates a partial vacuum, thereby drawing manifold gases at the periphery of venturi jet 18 and funneling them through venturi 16 to mix with the manifold gases flowing out horn 20.

The air extractor uses a jet of high-pressure motive gas to entrain lower pressure gas or suction gas that fills the manifold, thereby mixing the two gases thoroughly, and discharges the resulting gas combination at an intermediate pressure. The air ejector will operate with any motive gas. Motive gases can be steam, air, inert nitrogen or other gas or mixture such as compressed air. Thus, where a confined space is remote from electrical power, steam or bottled compressed gas can develop the necessary motive gas stream and hence the vacuum. In addition, where compressed air, steam, or bottled gas is used, the flow of motive gas will not introduce an ignition source to the sampled gas. It is important to note that the operator may select the particular high-pressure gas used to create the vacuum. Because the venturi not only draws the manifold gas but also mixes the high-pressure motivating gas and the low-pressure manifold gas, circumstances of use might dictate the selection of motivating gas. For instance, where the suspected gas for sampling through the manifold is particularly flammable, the operator might choose nitrogen or one of the "noble gases" such as helium. Another circumstance that might dictate the choice of a particular gas would be the convenience of the operator. The selection of a bottled gas would allow use of the invention at a remote location, far away from a powered compressor. Similarly, where an operator suspects the presence of a flammable gas, a powered compressor might introduce an ignition source to the mixed gases with catastrophic results.

Each manifold port 32 of the sampling manifold assembly 30 corresponds to an attached hose (not shown) and, at the extreme end of the hose, a probe for sampling (not shown). The hose and probe assembly can be as simple as a hose with an open end. Alternate configurations of the probe and hose assembly allow the operator some selectivity in sampling gases within a space. For instance, if, as in a firefighting application, the operator wishes to test for the presence of hot combusted gases lighter than the ambient air, the probe might well stand at a height close to the overhead or ceiling within the sampled compartment. On the other hand, where an operator wishes to test the toxicity of the atmosphere at the bilges of a ship, the operator might mount the probe on a buoy, thus sampling the gas from the lower extreme of the atmosphere present in the bilge. This application does not seek to claim the probe and hose but rather presumes the existence of such a hose and probe, suitably placed to sample such gas as is present in the suspect location.

When in use, an operator can selectively sample atmospheric gases in distinct locations by opening and closing manifold port valves 36. For instance, vessel Incident Commanders can selectively sample the atmosphere certain vessel compartments during shipboard fires by knowing the location of probes placed within the vessel and their corresponding valves on the manifold. When the operator opens one of the manifold port valves, vacuum within the manifold draws atmospheric gas through the probe and hose attached to the manifold port valves and manifold ports 34, into the manifold. When the manifold port valve is open for a sufficient time for the gas to travel the length of the hose, the gas contained in manifold 32 duplicates that present at the probe. Once the manifold body is full, the operator simultaneously closes manifold port valve 36 and motivating gas inlet valve 14, trapping a large sample of the suspect gas in the manifold.

Once the suspect gas is trapped in manifold 32, the operator attaches the intake hose of a commercially available gas-sampling device (not shown) to sampling ports 38. The commercially available gas-sampling device draws and analyzes the sample contained within the manifold. Because horn 20 vents to the atmosphere, the commercially available gas-sampling device can draw a pure column of the sample without applying extraordinary vacuum. The present invention can readily be adapted to accommodate the particular desired dimensions of the gas column to the intended gas-sampling device.

The present invention further anticipates incorporation of additional sensors beyond the gas-sampling device. While not necessary to the instant invention, a thermocouple, thermopile, or thermometer used in conjunction with the disclosed invention would yield additional useful information pertaining the sampled gas. The temperature sensing capability would also protect the instant invention from extremes that might damage the invention or the gas-sampling device. When so indicated by the temperature sensor, flushing the manifold with ambient air would serve to cool invention as well as to remove sampled gas.

In addition to obvious safety benefits, the present invention derives usage, durability, portability, and manufacturing advantages associated with the simplicity of its design. There are no moving parts in the instant invention. The only critical part-to-part relationship or tolerance in the invention is within the air extractor and, due to the simplicity of design, a manufacture can machine this extractor from a single casting. Cleaning and repair are easy, even without the benefit of a skilled technician.

The lack of moving parts makes the invention durable as well. Because the dimensions of the venturi jet and the velocity of the motive gas determine the vacuum the air extractor produces, the manufacturer is free to select such materials as will hold up in the presence of likely suction and motive gases. Where the sampling manifold will be carried to the worksite, the manufacturer can further narrow the selection of materials to those known to withstand potentially physical use common on an industrial site. In short, the simplicity of the invention provides great latitude in selecting the component parts. Plumbing brass has proven suitable to firefighting applications by allowing the fabrication of the invention from off-the-shelf parts, except the venturi jet. The availability of such parts further reduces costs typically associated with gas sampling equipment.

At the manifold, several features contribute to the overall simplicity of the invention. As displayed in the accompanying diagrams, the preferred embodiment of the present invention uses numerous independent valves to selectively expose various hoses and their attendant probes to the extractor-generated vacuum. The samples drawn through the hoses are only useful to the extent that they correspond to separate and distinct locations. Mixing of sampled gases is not useful. Therefore, in an alternative embodiment, a single ganged valve could substitute for the several independent valves and would only expose a single hose or port to vacuum. In either embodiment, the generated vacuum will only draw though a single port at a time. Thus because there is no concern over dilution of the vacuum, there is no practical limit to the number of sampling hoses a single manifold might service.

Figure 2:
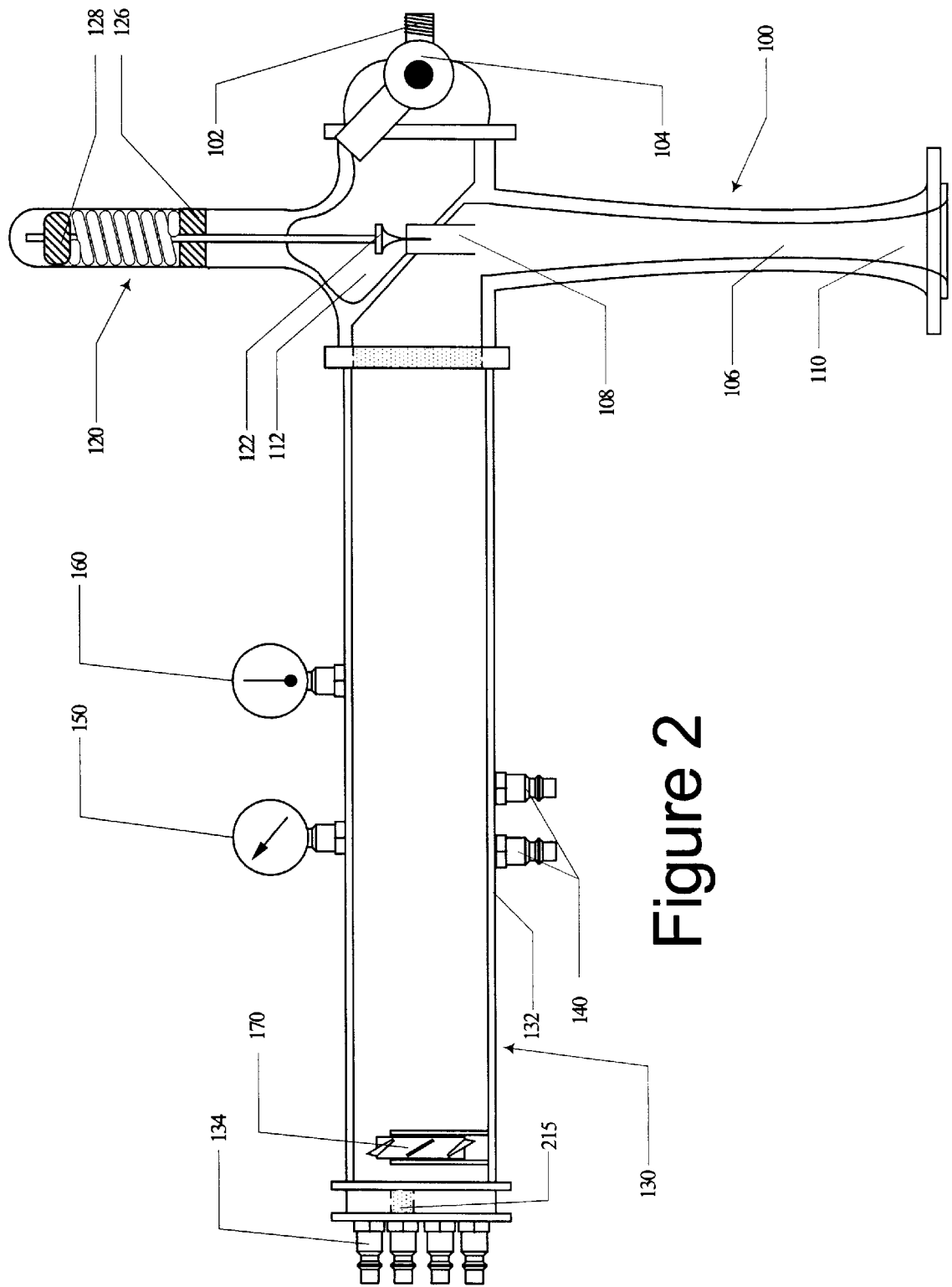
FIG. 2 is a second embodiment of the present invention, including a regulator assembly.

FIG. 2 illustrates an alternative embodiment of the invention. Like the above-identified preferred embodiment, it comprises in combination an air extractor assembly 100 and a sampling manifold assembly 130. Air extractor assembly 100 includes an inlet port 102 with an associated inlet valve 104 for selectively interrupting the flow of gas through the inlet port, a venturi 106 having on one end to a venturi jet 108 and on the other end to a horn 110, and a plenum 112. The air extractor assembly further includes a regulator assembly 120 used to control the volume of motivating gas that flows through venturi jet 108. The needle assembly 120 includes a needle piston 122 in the throat of the venturi jet 108 used to control the volume of motivating gas that flows through the venturi jet. The needle piston is connected to a regulator spring 124 having a lower stop 126 and an upper spring stop 128. The speeding motivating gas passing between the walls of the throat of the venturi jet creates a localized low-pressure zone that draws the needle piston into the throat of the venturi jet. The needle piston pulls against upper spring stop 128, which draws the upper spring stop against the controlled pressure of the regulator spring. The regulator spring rests upon lower stop 126 fixed in relation to plenum 112. The relationship between the compressive tension of the regulator spring and the draw of the needle piston results in a stable equilibrium. With due care, one skilled in the art may select that stable equilibrium so as to optimize the flow of motivating gas and create the greatest vacuum with the least expenditure of motivating gas.

Sampling manifold assembly 130 includes a manifold 132 and one or more manifold ports 134. FIG. 2 shows an alternate embodiment to the manifold port valves 36 of the embodiment of FIG. 1. As indicated in the discussion above, the vacuum generated by the air extractor can drive extraction through only one manifold port 134 at a time. Multiple manifold ports open simultaneously means more gas rushing in to compromise the vacuum, which in turn results in blending gases from two different locations. This gives imprecise information about the sampling areas. Thus, in this embodiment, a manifold plate 136 is placed between the manifold ports and the manifold, the manifold plate having a hole that can be aligned between the manifold and any single manifold port to allow flow between the manifold port into the manifold. Use of the manifold plate and adjustable manifold port hole prevents the simultaneous opening of more than one manifold port 134; the manifold port hole can either align with one of the manifold ports 34 or stop in the intermediate space between manifold ports, thereby stopping all flow between the manifold ports and the manifold. This alternative embodiment achieves the several advantages set forth above related to the manner in which it operates. The sampling manifold assembly further includes one or more sampling port 140.

It will be appreciated by those skilled in the art that the location and number of manifold ports and sampling ports may vary without departing from the scope of the present invention. For instance, the manifold ports 134 with the associated manifold plate 136 shown in position at the end of the invention as embodied in FIG. 2 might substitute for the several manifold ports 34 and their attendant manifold valves 36 along the top of the invention as embodied in FIG. 1.

The air extractor in the embodiment shown in FIG. 2 has an additional capability not present in the above-identified preferred embodiment. As in the embodiment in FIG. 1, high-pressure gas enters the air extractor assembly through inlet port 102. A motivating gas feed valve 104 interrupts the fed motivating gas and the resultant vacuum. Plenum 112 does not necessarily pass through or cool the body of the gas manifold 130. By virtue of regulator assembly 120, the venturi jet in this embodiment enjoys a particular refinement not present in the embodiment in FIG. 1, namely, the ability to regulate the flow of motivating gas in response to pressure variations within the plenum.

The vacuum generated by the air extractor drops the pressure in manifold 132. It is sometimes beneficial to monitor the pressure within the manifold. An alternative embodiment of the present invention therefore includes a pressure gauge 150, which displays the vacuum level within the manifold. While the pressure gauge is not necessary for the efficacy of the invention, the information it displays is useful to the operator. For instance, the pressure gauge would report that the air extractor failed to create a vacuum in response to opening the motivating gas inlet valve 104. Similarly, if a probe was blocked or a hose crimped, the pressure gauge would indicate the absence of a rise in pressure as the operator opened the corresponding manifold port 134. The free flow of sample gas from the manifold port 134 into the manifold should compromise the vacuum held in the manifold resulting in an intermediate reading between atmospheric pressure and that of the partial vacuum created by the extractor against a closed manifold.

FIG. 2 shows the addition of another component of the alternative embodiment, namely, a temperature gauge 160. The temperature gauge may be a bimetal strip, a thermopile, or a thermocouple. The purpose of the temperature gauge is to approximate the temperature of the gas in manifold body 132. While this temperature gauge is not a precise means of measuring temperatures at the probes because the hoses will dissipate much of the heat contained in the sample gas, it nonetheless gives a general and useful indication of the pertinent temperature. A significantly elevated temperature might indicate that the sampled gases are by-products or in close proximity to combustion. Such information would significantly inform the efforts of firefighters or workers in an industrial environment of potential hazards.

FIG. 2 shows still another additional component, an integrated flow meter 170. The meter shows the flow of sample gas drawn into the sampling manifold. Like the temperature of the sampled gas, the precise volume of sampled gas is not a necessary measurement. Rather, the purpose of the flow meter is to assure a complete purge of the hose and probe (not pictured) and the delivery of a recent sample from the proximity of the probe.

While the preferred embodiment of the invention has been illustrated and described, as noted above, many changes can be made without departing from the spirit and scope of the invention. For example, the invention need not be portable. Given the simple and reliable nature of the invention, the construction might include the permanent installation of probes and conduit hoses in holds of ships, silos, or materials handling spaces much as those same spaces contain sprinkling systems today. Additionally, such construction might afford the designation of a command center where the venturi-based gas-sampling manifold of the present invention is permanently affixed to those hose conduits. In yet another example, servos could control all of the valves within the invention. Automated control of the servos and hence the valves would allow constant intermittent sampling of all spaces where probes are present. Additional automation with an interface with the gas sampling machinery would allow the logging of test results in each of the corresponding probe locations. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A system for extracting and conveying sampling gases from a remote location for component and quality testing by a gas-sampling device by use of a venturi-based manifold that moves a volume of motivating gases to create a venturi effect, comprising:
   an air extractor for creating a vacuum to draw sampling gases for testing, the air extractor comprising:
   a venturi having an inlet end and an outlet end;
   an inlet port into through which the volume of motivating gases is drawn; and
   a plenum extending from the inlet port to the inlet end of the venturi;
   a manifold for testing the sampling gases drawn by the air extractor, the manifold comprises:
   a housing defining a chamber;
   at least one manifold port through which the sampling gases from the remote location are drawn into the housing by the venturi effect created by the air extractor; and
   at least one sampling port through which a sample of the sampling gases drawn by the air extractor into the housing of the manifold are drawn by the gas-sampling device; and
   a pressure gauge for monitoring and reporting the pressure of the gases within the manifold.

2. The system of claim 1, further comprising a venturi jet at the inlet end of the venturi through which the volume of motivating gas is drawn to create a venturi effect.

3. The system of claim 1, further comprising a horn at the outlet end of the venturi through which motivating gases are vented to the atmosphere.

4. The system of claim 1, further comprising an inlet valve for selectively interrupting the flow of motivating gases through the inlet port into the plenum.

5. The system of claim 1, further comprising a manifold port valve for selectively interrupting the flow of sampling gases through the manifold port into the manifold.

6. The system of claim 1, further comprising an adjustable manifold plate between the manifold and the manifold port, the manifold plate having a hole that can be aligned between the manifold and the manifold port to allow flow of sampling gases from the manifold port into the manifold.

7. The system of claim 1, further comprising a sampling port valve for selectively controlling the sample of sampling gases from the manifold to the gas-sampling device.

8. The system of claim 1, further comprising a temperature gauge for monitoring and reporting the temperature of the gases within the manifold.

9. A method for extracting and conveying sampling gases from a remote location for component and quality testing by a gas-sampling device by use of a venturi-based manifold that moves a volume of motivating gases to create a venturi effect, comprising:
   feeding high-pressure motivating gases through a venturi to create a venturi effect;
   extracting and conveying sampling gases from a remote location by use of the venturi effect created by the venturi;
   drawing sampling gases into a manifold through a manifold port;
   testing samples of the sampling gases from the manifold using the gas-sampling device;
   venting the sampling gases from the manifold; and
   monitoring and reporting the volume of the gases flowing through the manifold by use of a flow meter.

10. The method of claim 9, wherein the sampling gases are extracted and conveyed from a remote location into the manifold via the manifold port, and wherein the step of extracting and conveying sampling gases from a remote location by use of the venturi effect created by the venturi further comprises selectively interrupting the flow of sampling gases through the manifold port into the manifold using a manifold part valve.

11. The method of claim 9, further comprising monitoring and reporting the temperature of the gases within the manifold by use of a temperature gauge.

12. A method for extracting and conveying sampling gases from a remote location for component and quality testing by a gas-sampling device by use of a venturi-based manifold that moves a volume of motivating gases to create a venturi effect, comprising:
   feeding high-pressure motivating gases through a venturi to create a venturi effect;
   extracting and conveying sampling gases from a remote location by use of the venturi effect created by the venturi;
   drawing sampling gases into a manifold through a manifold port;
   testing samples of the sampling gases from the manifold using the gas-sampling device; and
   venting the sampling gases from the manifold,
   wherein feeding high-pressure motivating gases through a venturi to create a venturi effect further comprises controlling the operation of the venturi by positioning a needle piston movably with respect to the venturi to control the volume of motivating gas that flows through the venturi and create the greatest vacuum with the least expenditure of motivating gas.

13. A method for extracting and conveying sampling gases from a remote location for component and quality testing by a gas-sampling device by use of a venturi-based manifold that moves a volume of motivating gases to create a venturi effect, comprising:
   feeding high-pressure motivating gases through a venturi to create a venturi effect;

extracting and conveying sampling gases from a remote location by use of the venturi effect created by the venturi;

drawing sampling gases into a manifold through a manifold port;

testing samples of the sampling gases from the manifold using the gas-sampling device;

venting the sampling gases from the manifold; and monitoring and reporting the pressure of the gases within the manifold by use of a pressure gauge.

14. A system for extracting and conveying sampling gases from a remote location for component and quality testing by a gas-sampling device by use of a venturi-based manifold that moves a volume of motivating gases to create a venturi effect, comprising:

an air extractor for creating a vacuum to draw sampling gases for testing, the air extractor comprising:

a venturi having an inlet end and an outlet end;

an inlet port into through which the volume of motivating gases is drawn; and a plenum extending from the inlet port to the inlet end of the venturi; and a manifold for testing the sampling gases drawn by the air extractor, the manifold comprises:

a housing defining a chamber;

at least one manifold port through which the sampling gases from the remote location are drawn into the housing by the venturi effect created by the air extractor; and at least one sampling port through which a sample of the sampling gases drawn by the air extractor into the housing of the manifold are drawn by the gas-sampling devices, wherein the air extractor further includes a regulator assembly used to control the operation of the venturi, comprising:

a needle piston movably positioned with respect to the venturi that is used to control the volume of motivating gas that flows through the venturi; and a regulator spring connected to the needle piston for adjusting the needle piston with respect to the venturi to optimize the flow of motivating gas and create the greatest vacuum with the least expenditure of motivating gas.

15. A system for extracting and conveying sampling gases from a remote location for component and quality testing by a gas-sampling device by use of a venturi-based manifold that moves a volume of motivating gases to create a venturi effect, comprising:

an air extractor for creating a vacuum to draw sampling gases for testing, the air extractor comprising:

a venturi having an inlet end and an outlet end; an inlet port into through which the volume of motivating gases is drawn; and a plenum extending from the inlet port to the inlet end of the venturi;

a manifold for testing the sampling gases drawn by the air extractor, the manifold comprises:

a housing defining a chamber;

at least one manifold port through which the sampling gases from the remote location are drawn into the housing by the venturi effect created by the air extractor; and at least one sampling port through which a sample of the sampling gases drawn by the air extractor into the housing of the manifold are drawn by the gas-sampling device; and a flow meter for monitoring and reporting the volume of the gases flowing into the manifold.

* * * * *